United States Patent [19]

Hausman Hazlitt et al.

[11] Patent Number: 4,996,160
[45] Date of Patent: Feb. 26, 1991

[54] METHOD AND APPARATUS FOR QUANTITATIVE MEASUREMENT OF IONIC AND ORGANIC CONTAMINANTS REMAINING ON CLEANED SURFACES

[75] Inventors: Andrea J. Hausman Hazlitt; Warren F. Richey, both of Lake Jackson, Tex.

[73] Assignee: The Dow Chemical Company, Midland, Mich.

[21] Appl. No.: 60,136

[22] Filed: Jun. 9, 1987

[51] Int. Cl.$^5$ .................... G01N 21/27; G01N 21/51; G01N 31/00
[52] U.S. Cl. ........................... 436/2; 156/626; 156/627; 324/71.1; 356/319; 422/82.02; 422/82.06; 422/82.09; 436/149; 436/150; 436/177
[58] Field of Search ............... 422/82.02, 82.06, 82.09; 436/2, 149, 150, 177; 156/626, 627; 324/71.1; 356/319

[56] References Cited

U.S. PATENT DOCUMENTS

| | | | |
|---|---|---|---|
| 3,973,572 | 8/1976 | Brous | 134/57 R |
| 4,023,931 | 5/1977 | Wolfgram | 436/150 |
| 4,530,601 | 7/1985 | Tasset . | |
| 4,731,154 | 3/1988 | Hausman Hazlitt et al. | 156/626 |

OTHER PUBLICATIONS

W. F. Richey, et al., "New Analyses for Residual Rosin on Cleaned Electronic Circuit Boards", *Proc. Nepcon West '85*, Feb. (1985), 301–303.
L. J. Turbini et al., "A Comparison of Removal of Activated Rosin Flux by Selected Solvents", *IPC*, Sep. (1979).
E. Westerlaken, "Rosin Solder Flux Residues Shape Solvent Cleaning Requirements" *Electronic Packaging & Production*, Feb. (1985) pp. 118–174.
C. F. Coombs, Jr. *Printed Circuits Handbood*, 2nd Ed. McGraw-Hill Book Co., 1979 pp. 16–17 to 16–18.
H. H. Manko, "New Packaging Tecniques Force a Reexamination of Cleaning Methods", Electronic Packaging & Production, Aug. (1984), 68–73.

S. L. Spitz, "Cleaning Printed Circuit Boards for Higher Quality: Electronic Packaging and Production", Sep. (1985), 100–106.
N. MacLeod, "The Rapid Testing of Ionic Contamination on Printed Wiring Boards and Assemblies", *Proc. Nepcon West*, vol. 1, Feb. (1986), 198–206.
J. K. Bonner, "A New Solvent for Post-Solder Cleaning of Printed Wiring Assemblies", Proc. Nepcon West, vol. 2, Feb. (1986), 763–774.
R. Aspandiar, et al., "Is OA OK?", Circuits Manufacturing Apr. (1986), 29–36.
Operating Manual for the Alpha Ionograph ® System.
H. Cole, "Measurement of Surface Ionic Contamination" Society of Manufacturing Engineers, (1975), AD 75-366, 1–12.
Alpha Metals, Inc., 1983, Brochure.
Federated-Fry Metals, Inc., Bulletin 201, Feb. (1985).
W. G. Kenyon, "How to Use the Solvent Extract Method to Measure Ionic Contamination of Printed Wiring Assemblies", Insulation Circuits, Mar. (1981), 47–49.

(List continued on next page.)

*Primary Examiner*—Robert J. Warden
*Assistant Examiner*—Jill Johnston

[57] ABSTRACT

An apparatus and method are used for determining the cleanliness of an electronic circuit assembly (ECA) such as printed circuit boards (PCB) following noraml cleaning and flux removal processes. The apparatus and method are used to quantitatively measure the ionic and organic contaminants remaining on an ECA. The apparatus utilizes small volumes of isopropanol, a conductivity/resistivity probe and cell and a spectrophotometric analytical instrument. The apparatus generally provides for washing the "cleaned" of defluxed ECA with a measured volume of isopropanol and thereafter measuring the ionic and organic contaminantts in the wash solution. The results can then be compared to a standard.

37 Claims, 6 Drawing Sheets

OTHER PUBLICATIONS

Kenco Alloy & Chemical Co., Inc., Omega Meter ® II System, Bulletin 379.

Kenco Alloy & Chemical Co., Inc., Omega Metal ® II Model 300, Operators Manual, 1979.

R. J. DeNoon, et al., "Detection of Ionic Contaminants on Printed-wiring Assemblies", Naval Avionics Facility MRR No. 3-72.

Institute of Printed Circuity, Test Methods Manual, No. 2.3.38 1/83, 1-5.

Institute of Printed Circuits, Test Methods Manual, No. 2.3.39 1/83, 1-7.

D. Sanger et al., "A Study of Solvent and Aqueous Cleaning of Fluxes", Naval Weapons Center, NWC TP 6427, Feb., 1983, pp. 1-108.

Guided Wave, Inc., The Optical Waveguide Spectrum Analyzer.

METHOD AND APPARATUS FOR QUANTITATIVE MEASUREMENT OF IONIC AND ORGANIC CONTAMINANTS REMAINING ON CLEANED SURFACES

BACKGROUND OF THE INVENTION

This invention relates to a method and apparatus for substantially simultaneously measuring the ionic and organic contamination of an electronic assembly, for example a printed circuit board.

The cleanliness of electronic circuit assemblies (ECA) such as printed circuit boards (PCB) is generally regarded as being critical to their functional reliability. Ionic and nonionic contamination on circuit boards are believed to contribute to premature failures of the circuit boards by allowing short circuits to develop.

In the manufacture of electronic circuit assemblies, ionic and nonionic contamination can accumulate after one or more steps of the process. Circuit board materials are plated, etched, handled by operators in assembly, coated with corrosive or potentially corrosive fluxes and finally soldered. Of course, there is cleaning at various steps along the way—for example after plating, etching and soldering—but each step, nevertheless, represents a potential source of ionic and nonionic contamination which may be carried over on surfaces of the finished circuit. It is therefore most important that a thorough cleaning of the surfaces be achieved after soldering. This is probably the last opportunity to remove ionic and nonionic contamination accumulating on the circuit in the manufacturing processes.

It is common to evaluate the level of ionic contamination on an assembled board by a solvent extraction test. The board to be tested is washed with an isopropanol/water mixture which is then subjected to an electrical conductivity/resistivity measurement from which an ionic concentration is calculated and expressed as a quantity of sodium chloride per unit area of board surface.

Until now there has been no simple quantitative analysis for both the ionic and nonionic contaminants or other organic contaminants such as residual rosin flux, on a cleaned ECA. "Organic contaminants" herein includes ionic and nonionic contaminants which are not detectable by conductivity/resistivity measurements known for measuring ionic contamination. In order to better study the effectiveness of various solvents in removing the ionic and nonionic contaminants from soldered boards, it is desired to provide a method and apparatus for determining both the ionic and nonionic contaminants down to concentrations of about 1 microgram per square inch.

SUMMARY OF THE INVENTION

One aspect of the present invention is a method for automatically and quantitatively measuring ionic and organic contamination on electronic circuit assemblies (ECA) comprising:

(a) contacting a previously defluxed ECA with a solvent adapted for removing ionic and organic contaminant species on the surface of the ECA, (b) substantially simultaneously measuring the spectral absorbance, in the ultraviolet or the visible region, of the organic contaminant species in the solvent contacted with the ECA and the conductivity/resistivity of the solvent contacted with the ECA, and (c) comparing the resultant absorbance and conductivity measurements to a standard.

Another aspect of the present invention is an apparatus for automatically and quantitatively measuring ionic and nonionic contamination such as residual rosin on electronic circuit assemblies (ECA) comprising:

(a) a vessel adapted for receiving an ECA and receiving a solvent for washing the ECA;

(b) a means for recirculating solvent to the vessel;

(c) a UV monitor adapted for receiving a sidestream of the recirculated solvent and adapted for measuring the absorption levels of the contaminants in the sidestream;

(d) a means for measuring the conductivity/resistivity of the recirculated solvent or sidestream of the recirculated solvent; and (e) a recorder means for recording the conductivity of the solution and the absorbance of the sidestream.

BRIEF DESCRIPTION OF THE DRAWINGS

The invention will be better understood by reference to the FIGS. 1-6 herein wherein the preferred embodiments of the present invention are illustrated and wherein like reference numerals refer to like parts in the different figures.

FIG. 1 is a schematic illustration of the apparatus of the present invention.

DETAILED DESCRIPTION OF PREFERRED EMBODIMENTS

Figure 4:
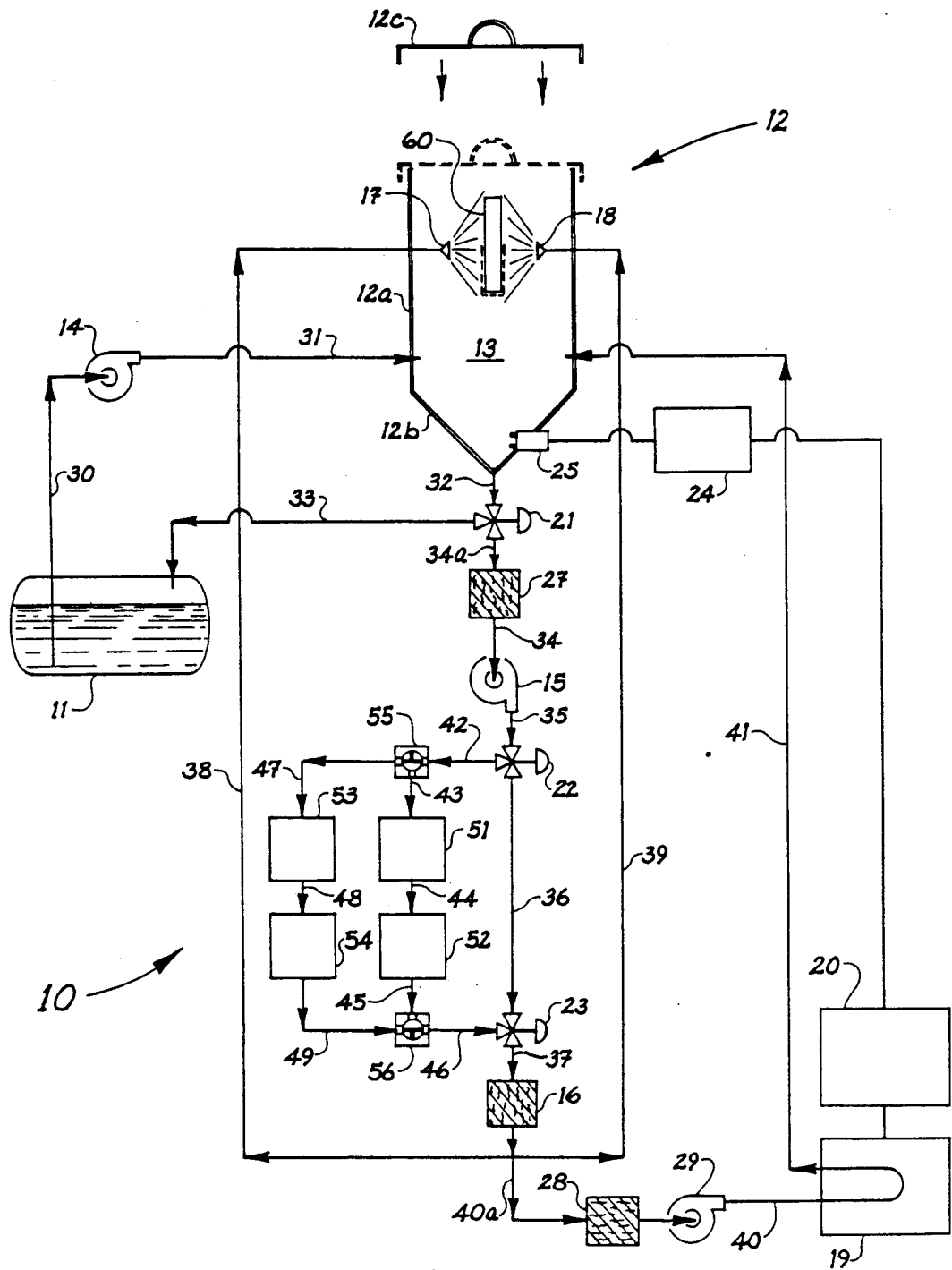
FIG. 4 is a schematic illustration of another embodiment of the apparatus of the present invention.

A general embodiment of the present invention is illustrated in FIG. 1 which shows an apparatus, generally indicated by numeral 10, which automatically and quantitatively measures the ionic and nonionic contamination, for example, on electronic circuit assemblies which have been cleaned or defluxed after the soldering steps in their manufacture. A solution reservoir 11 containing a solvent suitable for washing an ECA is connected, in fluid communication, to a vessel, generally illustrated by numeral 12 containing a chamber 13 adapted for receiving a test sample of specimen 60 of an ECA to be evaluated.

The shape of the vessel 12 may be any shape desirable for inserting an ECA such as a printed circuit board. The vessel 12 is preferably a cylindrical-shaped housing or tank 12a with a cone-shaped bottom portion 12b and a removable liquid tight cover 12c.

A measured quantity of liquid from the reservoir 11 is conducted to the vessel 12 via conduits 30 and 31 using a means for adding an accurately measured volume of solvent to chamber 13, in this instance a metering pump 14. The solvent from the chamber 13 can be removed from the vessel 12 through conduit 32 and diverted by a valve 21 to conduit 33 back to the reservoir 11 as shown in FIG. 1. In the alternative, the solvent can be discarded to a drain line (not shown). When the liquid from the chamber 13 is not recirculated back to the reservoir 11, it passes through conduit 34 to a pump 15.

The pump 15 is used for recirculating the solution in the chamber 13. From pump 15 and through conduit 35, the liquid passes through a valve 22, which can divert flow through conduit 42 and absorption beds 51 and 52 (described below), or can pass the liquid through conduit 36 to a valve 23 and to a filter 16. The solution is filtered by the filter 16 to remove any particles in the solution and to prevent plugging of spray nozzles 17 and 18 and a relatively small line 40 leading to the UV monitor 19. The liquid passing through the filter 16 is circulated from the vessel 12 via the recirculation loop consisting of conduits 32 and 34-39, inclusive, to the spray nozzles 17 and 18. Any number of spray nozzles and conduits from the recirculation pump 15 may be incorporated into the vessel 12. The spray nozzles 17 and 18 spray solution on the surface of the ECA to solubilize surface contamination.

Prior to inserting a specimen ECA 60 in chamber 13 for measurement of the contamination on the ECA, the measured amount of solvent in chamber 13 is treated to remove any residual ionic or nonionic substances which may be contained in the small amounts of liquid left over from any previous measurements. The valve 22, via conduits 42, 43 and 44, is used to divert flow into and through columns 51 and 52 for treating the solvent. Column 51 contains absorbent material, such as activated charcoal, to remove organics from the solvent and column 52 contains absorbent material, such as ion exchange resins, to remove ionics from the solvent. The valve 23 is used to return flow from columns 51 and 52 to conduit 37.

The sidestream 40 of the solution is conducted to a UV monitor 19 which is, preferably, connected to a recorder 20 for recording the output of the monitor. The monitor 19 is adapted for measuring the absorbance of certain organic contaminants, such as rosin, which may be present in the wash solution. The liquid continuously flows from the monitor 19 to the vessel 12 via conduit 41.

The solution circulated through the vessel continuously removes remaining contamination from the ECA 60 which is sensed by the UV monitor 19 and is recorded by a signal sensing means 20 connected to the monitor; the liquid circulates through the vessel to remove any remaining contamination until the reading as indicated by the recording means 20 reaches a substantially constant value. This constant value is the UV absorbance of the solution which is directly related to the level of contamination on the ECA 60 as shown in the calibration curve in FIG. 5.

A conductivity/resistivity detector 24 and a conductivity/resistivity cell or probe 25 is placed in vessel 12 for measuring the ionic contamination removed from the specimen ECA 60 and which is present in the solution in chamber 13. The results of the ionic measurements can be communicated to and recorded by the recording means 20 just as the results of the UV absorbance measurements are communicated to and recorded by the same recording means 20. The liquid is circulated through the vessel to remove any remaining contamination until the reading indicated on the recording device 20 reaches a substantially constant value. This constant value is the conductivity/resistivity of the solution which is directly related to the level of ionic contamination the ECA 60 as shown in the calibration curve in FIG. 6.

The recording means 20 is conveniently a dual pen strip chart recorder. When the readings from the UV monitor 19 and the conductivity/resistivity detector 24 as recorded on the recording means 20 have reached a predetermined level or blank reading, the valves 22 and 23 are used to return flow to the recirculation loop consisting of conduits 32 and 34 to 39, inclusive, and by-pass the absorption columns 51 and 52. The pump 15 is turned off, causing the solution flow to stop. The lid 12c of vessel 12 is removed to allow insertion of the specimen ECA 60 for the determination or measurement of any ionic or organic contamination which may have remained on its surface following the cleaning or defluxing steps in its manufacture. After the lid 12c is replaced, the pump 15 is turned on and the solution is recirculated as described above. The spray nozzles in the recirculation loop spray solution onto the surface of the specimen ECA 60 to solubilize surface contaminants.

Upon completion of the measurement, the pump 15 is turned off, the specimen ECA 60 is removed from chamber 13, and the lid 12c replaced on the vessel 12. The solution may either be drained from the chamber 13 via valve 21 and conduits 32 and 33 back to reservoir 11 or, alternatively, discarded. If the solution is to be discarded, conduit 33 is disconnected from reservoir 11 prior to opening valve 21. In another embodiment the liquid in chamber 13 may be pumped through the absorbent columns 51 and 52 to remove ionic and organic contaminants to the predetermined desirable baseline levels, as measured by the UV monitor and the conductivity/resistivity detector, prior to being returned to the reservoir 11 via valve 21 and conduits 32 and 33.

Figure 2:
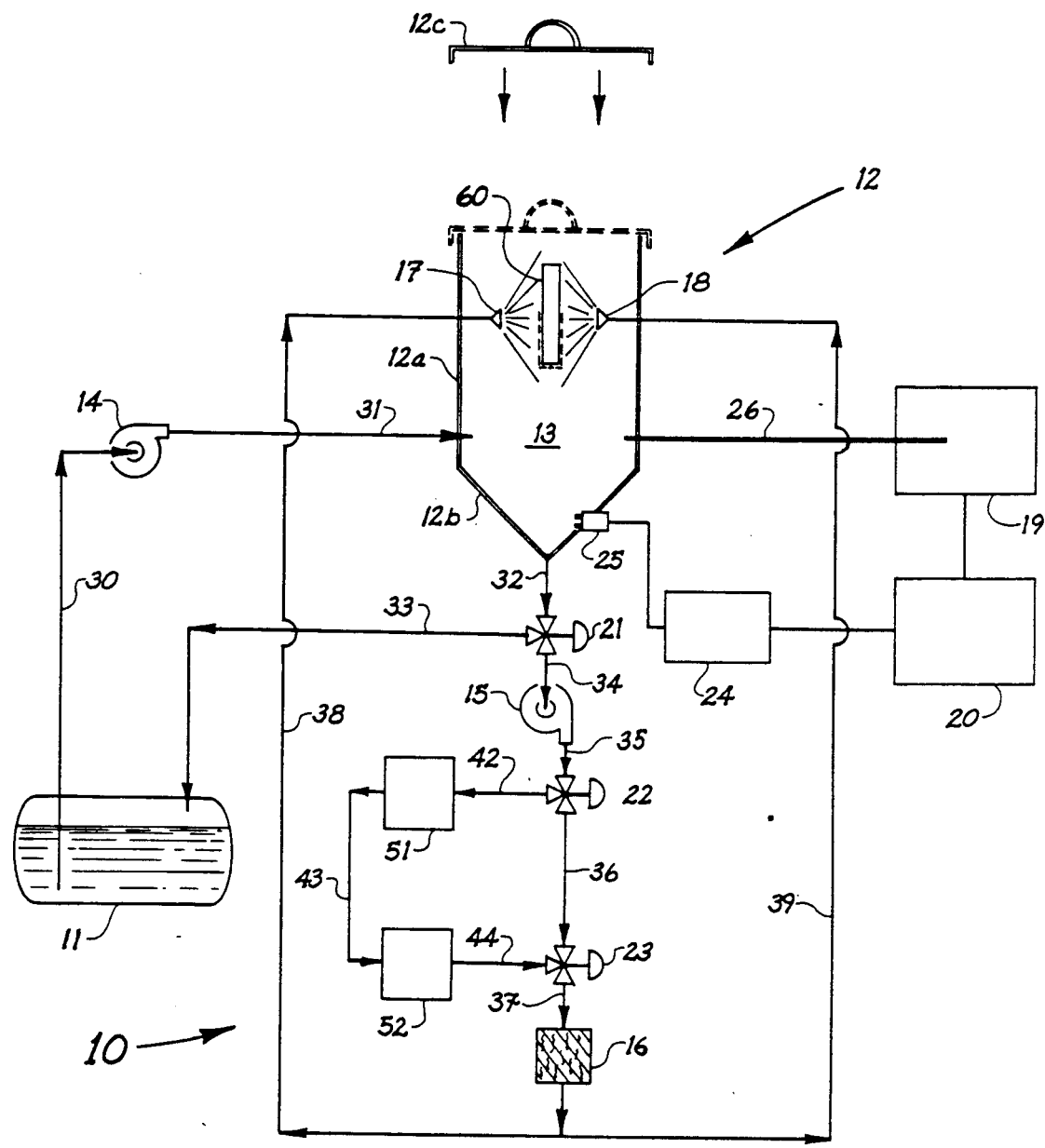
FIG. 2 is a schematic illustration of another embodiment of the apparatus of the present invention.

FIG. 2 shows another embodiment of an apparatus, generally indicated by numeral 10, which automatically and quantitatively measures the ionic and nonionic contamination, for example, on electronic circuit assemblies which have been cleaned or defluxed after the soldering steps in their manufacture. The apparatus of FIG. 2 is substantially the same as the apparatus of FIG. 1 except that in the embodiment of FIG. 2, a fiber optics probe 26 with cell for measuring absorbance of solution is inserted into chamber 13 below the liquid level in the region of low turbulence. The fiber optics probe 26, which is a alternative for the flow-through cell of the UV monitor of FIG. 1, is used to measure the absorbance of the organic contaminants in the solvent. In this embodiment, the apparatus and process is essentially the same as shown in FIG. 1 except that the lines 40 and 41 of FIG. 1 are not needed since the probe 26 communicates directly to monitor 19 and recorder 20.

Figure 3:
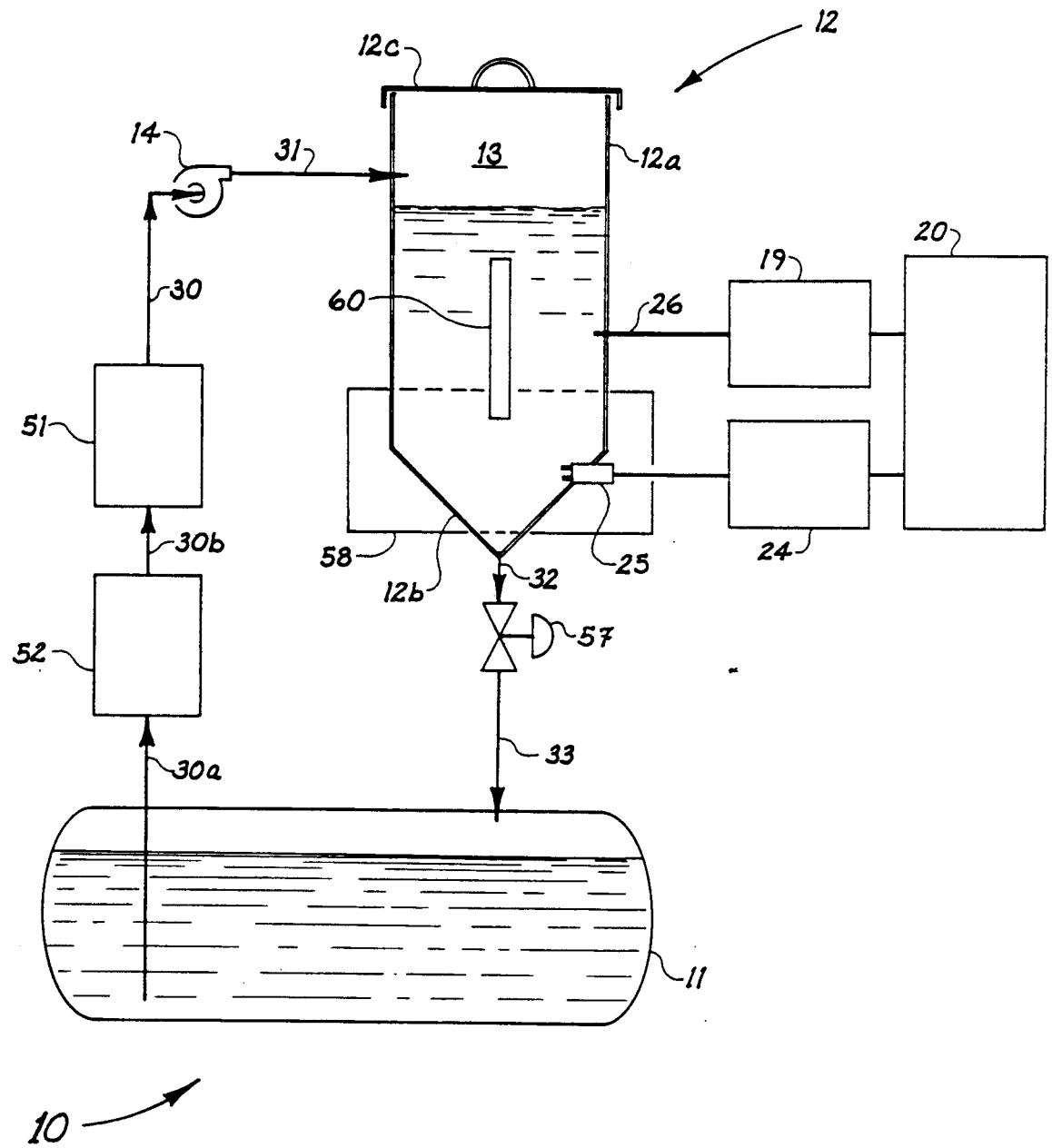
FIG. 3 is a schematic illustration of another embodiment of the apparatus of the present invention.
Figure 4:
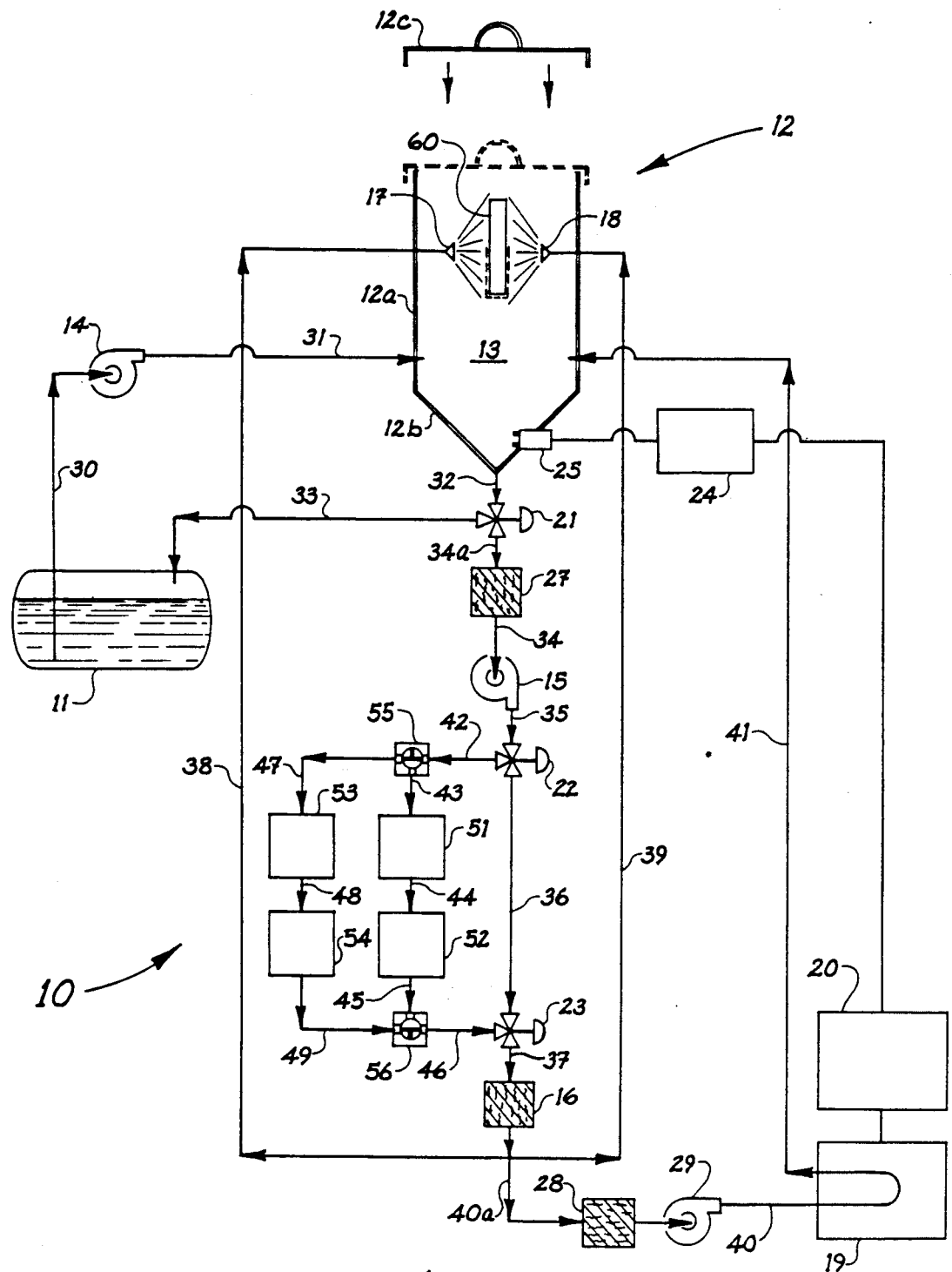

FIG. 3 shows another embodiment of an apparatus, generally indicated by numeral 10, which automatically and quantitatively measures the ionic and nonionic contamination, for example, on electronic circuit assemblies which have been cleaned or defluxed after the soldering steps in their manufacture.

A measured quantity of liquid (solvent) from the solution reservoir 11 is conducted to the vessel 12 via conduits 30a, 30b, 30 and 31, inclusive, using a means for adding an accurately measured volume of solvent to chamber 13, in this instance a metering pump 14. The solvent passes through columns 51 and 52 from the reservoir 11 and then through the metering pump 14 prior to entering the vessel 12. The measured amount of solution from the reservoir 11 in the vessel 12, may be recycled back to the reservoir using return lines 32 and 33 and through valve 57. In the alternative, the solution from vessel 12 can be discarded after passing through valve 57 to a drain (not shown).

The solution leaving the vessel 12 via conduit 32 may be filtered by a filter (not shown) to remove any particles in the solution if desired. The liquid in the vessel 12 is agitated by an agitation means 58 for example an ultrasonic generator or a magnetic stirring device requiring a Teflon coated bar magnet inside the chamber 13. The agitation is used to aid in solubilizing surface contamination on the surface of the ECA 60.

In the embodiment of FIG. 3, a fiber optics probe 26 with cell for measuring absorbance of the solvent is inserted into chamber 13 below the liquid level in a region of low turbulence. The fiber optics probe 26 is used to measure the organic contaminants in the solvent. Recording means 20 records the UV absorbance results from the fiber optics probe and interpreting device or detector 19.

A conductivity/resistivity detector 24 and a conductivity/resistivity cell or probe 25 is placed in vessel 12 for measuring the ionic contamination in the solution in chamber 13. The results of the ionic measurements can be communicated to and recorded by the recording means 20.

FIG. 4 shows another embodiment of the apparatus of the present invention, generally indicated by numeral 10, which automatically and quantitatively measures the ionic and nonionic contamination, for example, on electronic circuit assemblies which have been cleaned or defluxed after the soldering steps in their manufacture. While the other apparatuses, shown in FIGS. 1–3, are useful in carrying out the process of the present invention, the method shown in FIG. 4 is the most preferred embodiment.

The embodiment in FIG. 4 is substantially the same as the embodiment shown in FIG. 1 except that in the embodiment of FIG. 4, an additional filter 27 is positioned on the suction side of the pump 15 to protect the pump from damage by particulates entrained in the solution. In addition, a third filter 28 and a pump 29 is added in the sidestream 40 to prevent even smaller particles from plugging the realtively small diameter line to the UV monitor 19. Also, a second set of absorbent columns 53 and 54, with 53 containing absorbent material for organics similar to that in column 51 and 54 containing absorbent material for ionics similar to that in column 52, are included in the most preferred embodiment. Three-way valves 55 and 56 are used to alternatively select one set of columns while the other set is on standby. When columns 51 and 52 are being used the flow of liquid passes through conduits 42–46, inclusive, and flow through conduits 47–49, inclusive, is shut off by valves 55 and 56. When Columns 53 and 54 are being used, the flow of liquid passes through conduits 42, 47–49, and 46 and flow through conduits 43–45 is shut off by valves 55 and 56.

The method and apparatus described herein is useful in determining substantially simultaneously the ionic and nonionic contamination of electronic assemblies, for example printed circuit boards. Such boards are customarily cleaned after soldering operations, which cleaning operation is to remove as much as possible of the various contaminants which are caused by the soldering process. Such ionic and nonionic contamination can cause subsequent corrosion if not removed from the printed circuit board.

The processes used by the manufacturers of printed circuit boards normally will provide substantially clean boards. The present invention is directed to a means for testing the reliability of such cleaning processes.

In the present invention, absorption spectroscopy, particularly in the ultraviolet (UV) and visible regions, is the basis for the quantitative analysis of the organic contaminants present on the surface of ECA's. Any organic contaminant which is (1) soluble in a solvent which, in turn, is transparent in the portion of the ultraviolet or visible region of interest and (2) which absorbs energy in the ultraviolet or visible region of the spectrum may be quantified in accordance with the method and apparatus of the present invention. The maximum wavelength of the absorbing organic contaminant species is measured in the region of interest which may lie in the range of about 190 nanometers (nm) to about 800 nm.

Residual organic contaminants which are likely to be found on ECA and which can be measured by the method and apparatus of the present invention include, but are not limited to, for example, rosin flux, photoresist, solder masks, adhesives, machine oils, greases, silicones, lanolin, mold release, polyglycols and plasticizers. Generally, the organic contaminants of the present invention are nonionic. Some contaminants for example, abietic acid, measured by the present method may dissociate slightly in some solvents and therefore may be considered partially ionic. However, for purposes of measurement by the method of the present invention, the term "organic contaminants" includes such slightly ionic contaminants and other ionic contaminants which can not be measured or detected by conductivity/resistivity measurement known by those skilled in the art for measuring ionic contamination.

Examples of organic contaminants and their characteristic wavelengths are described below in Table I.

TABLE I

| Contaminant | Solvent | Wavelength (nm) |
|---|---|---|
| 1. photoresist Resiston ® made by DuPont De Nemours, E.I., Inc. | methylene chloride | 622 |
| 2. solder mask Wondermask ® made by Techspray of Amarillo, Texas | isopropanol | 220 plus weak band at 275 |
| Vacrel ® 930 made by DuPont De Nemours, E.I., Inc. | isopropanol | 226, 252 shoulders 278 and 282, broad weak bank centered on 350 |
| 3. adhesives rubber-based such as found on FasTape C ® made by Fasson Industrial Division of Avery International | isopropanol | 220 plus peak spikes at 265, 275, weak band at 410, shoulders at 240, 250 |
| silicone such as found on Kapton ® tape sold by 3M Co | isopropanol | 220, broad shoulder at 262 |
| 4. silicones adhesives (see above) rubber such as Silastic ® 732 RTV Dow-Corning Corp. | isopropanol (partially soluble) | broad band 235 to 220 |
| oil such as Fluid 200 made by Dow-Corning Corp | isopropanol | marked increase in baseline even at 400, increased slope between 300 and 200 , |
| 5. plasticizers such as found in polyethylene films/bags | isopropanol | increased slope in baseline at about 240 |

When referring to the organic or nonionic contaminant which can be measured by the method and apparatus of the present invention, the present invention will be described herein with regard to the measurements of rosin flux. Rosin fluxes consist primarily of natural gum rosin in an organic solvent. A major component of gum rosin is abietic acid which shows an ultraviolet absorbance maximum at about 242 nm, it being understood that published data sets the absorbance at 241.7 nm. This absorbance is the basis for the spectrophotometric method of determining the quantity of residual rosin on a cleaned, printed wiring assembly.

Common sources of ionic contamination on ECA include, for example, the chemical activators, such as quaternary ammonium halide salts, found in many of the rosin-based soldering fluxes; salts from fingerprints or perspiration of humans handling the ECA during its manufacture; and, rarely, metal salts from surface oxidation or chemical corrosion of some of the metallic features of the ECA.

In carrying out the preferred method of the present invention, with reference to FIG. 4, an accurately measured amount of solvent such as isopropanol is added to the vessel 12 from the reservoir 11 and flow through conduit 33 is closed via valve 21. A convenient quantity of solvent used may be from about 1 to about 20 ml per square inch of board, depending on the anticipated contamination level, with 10 ml per square inch generally preferred. Once the desired volume of fluid has been placed within the vessel, the pump 15 is started and the solution is continuously circulated through the vessel 12.

The UV absorbance of the solution is continuously monitored by the UV detector 19, and the electrical conductivity of the solution is continuously monitored by the probe 25 and ionic detector 24. Both measurements are recorded by recorder 20. If the readings are greater than predetermined desirable baseline levels, the solution is circulated through the absorbent cartridges 51 and 52 or 53 and 54 by opening valves 22, 55, 56 and 23 as needed. After the UV absorbance and conductivity readings for the solvent are satisfactory, valves 22 and 23 are reset so the solvent stream by-passes the absorbent beds 51-54 and flows through conduit 37 to filter 16. The liquid then passes through conduits 38 and 39 to spray nozzles 17 and 18 wherein the ECA specimen 60 is washed with solvent and contamination on the ECA is removed.

Substantially simultaneously a continuous sidestream 40 is conducted from the recirculation loop and the UV absorption or absorbent level of the contaminants in the wash solution is measured as the sidestream passes through a quartz tube cell of a UV monitor 19. The sidestream 40 is circulated back to the vessel via conduit 41. A recording means 20 is used to record the readings from the UV monitor 19. Also, substantially simultaneously, the conductivity of the solution is measured by the conductivity/resistivity detector 24 and cell or probe 25. The recording means 20 is used to record the readings from the conductivity/resistivity detector.

All of the equipment of the apparatus in contact with the solvent is preferably made of material which will not corrode or react with the solvent used in the process. Preferably, inert fluoropolymer or glass is used for the reservoir, vessel and the conduits; inert coatings can also be used. Stainless steel may contribute unwanted ionic substances which could give false, inaccurate or misleadingly high values for conductivity. Plastics which contain plasticizers may be subject to said plasticizers leaching from them by action of the solvent and/or may be susceptible to solvent stress cracking. The dissolved plasticizers may interfere with the UV absorbance measurements of organic/nonionic contaminants.

Figure 5:
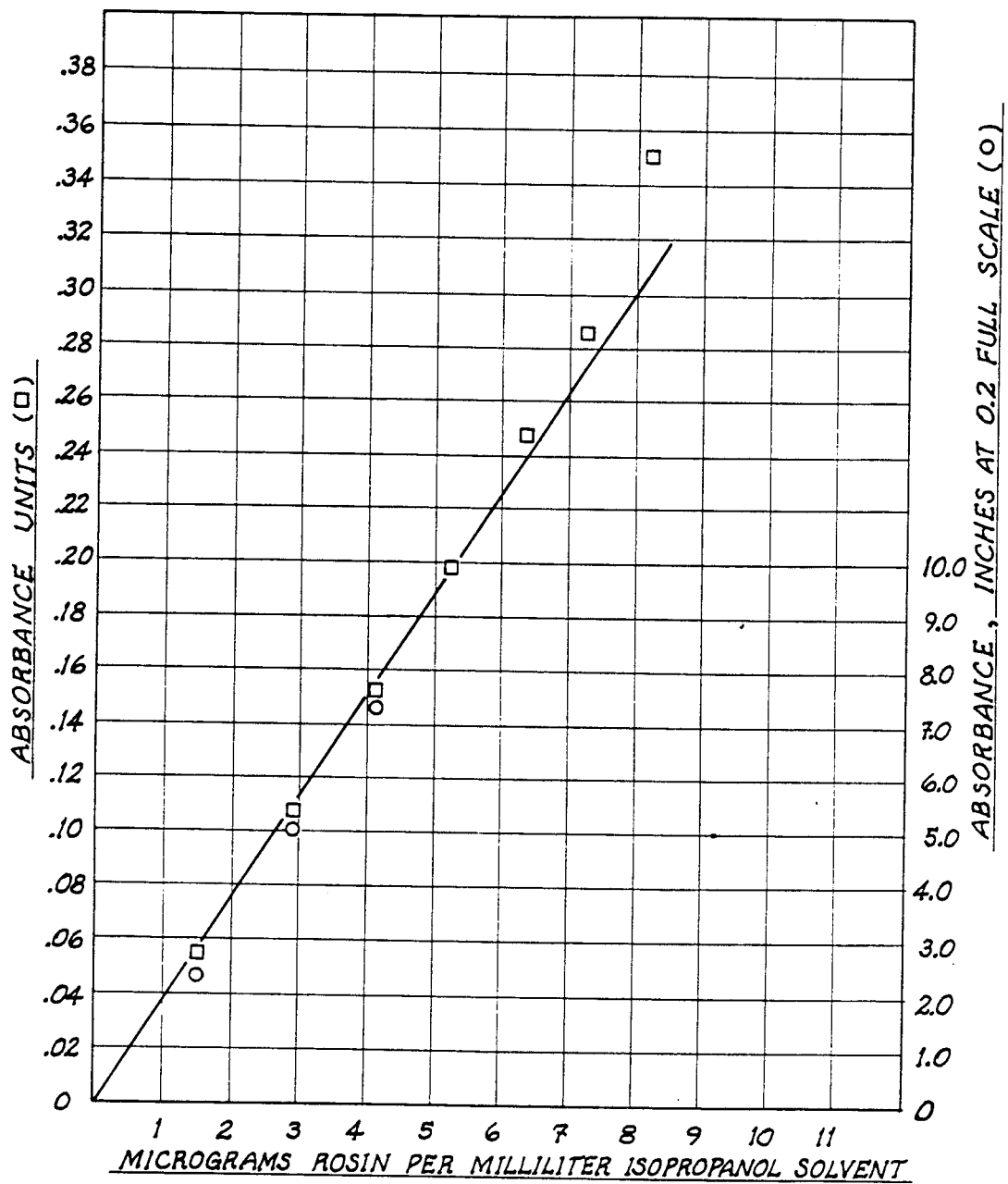
FIG. 5 represents a typical concentration rosin vs. absorbance calibration curve.

The absorbance of the wash solution at 242 nm is measured and compared to that on a standard curve of absorbance versus rosin concentration. FIG. 5 represents a typical ppm rosin calibration curve. The rosin concentration obtained from the standard curve is converted into a rosin contamination level in micrograms per square inch by use of the following equation:

$$\text{Residual organic contaminant}\left(\frac{\text{micrograms}}{\text{inch}^2}\right) = $$

$$\frac{\left[\text{organic contaminant concentration}\left(\frac{\text{micrograms}}{\text{gm solvent}}\right)\right] \times \left[\begin{array}{c}\text{solvent sp.}\\ \text{gr. or density}\\ \text{(gm/ml)}\end{array}\right] \times \left[\begin{array}{c}\text{vol solvent}\\ \text{(ml)}\end{array}\right]}{\text{total surface area of board (inch}^2)}$$

The minimum concentration of rosin which can be reliably measured by UV spectroscopy is about 1 ppm. The minimum volume of wash solvent is about 1 ml per square inch of board. Given these limitations, the minimum detectable level of rosin contamination is about 0.8 microgram per square inch. Improvements in spectroscopic technology could, of course, improve the sensitivity as could reducing the volume of solvent relative to board surface area.

A spectrophotometer capable of measuring absorption at about 242 nm is preferred for this analysis.

Solvents which are deemed suitable i.e. having the requisite UV transparency and solvency for the solids in addition to the well known and widely used isopropanol, either High Performance Liquid Chromatographic grade (HPLG) or Spectral Grade (SG), are ethanol, trifluoroethanol, as well as other polar solvents capable of dissolving at least abietic acid, and preferably all the organic solids of a flux formulation or other organic contaminants of interest, and having a boiling point (b.p.) preferably below about 100° C., but higher b.p. solvents could be used if application of heat is not detrimental, such as acetonitrile, isobutyl alcohol, methanol, propronitrile and if heat is not detrimental butyl alcohol, butyronitrile and, isopentyl alcohol. While solvents such as para-dioxane or ethyl ether may be used, the former may have toxicity problems and both the former and latter could create a fire hazard. The preferred solvent used in the present invention isopropyl alcohol (IPA).

A calibration curve for the ionic contamination on an ECA is constructed from data obtained by measuring the conductivity of an IPA solution containing a measured aliquot of a standard aqueous solution of sodium chloride (NaCl). The following equation is used to compute the final concentration of NaCl in the IPA solution.

$\mu$g NaCl/ml of test solution =

-continued $$\mu g\ NaCl/sq.\ in.\ calibration = \frac{[\text{concentration of standard } (\mu g\ NaCl/ml)] \times [\text{vol. standard } (ml)]}{\text{total volume of solution in chamber } (ml),\ \text{i.e., vol. standard} + \text{vol IPA/H}_2\text{O delivered to chamber}}$$

The conductivity of the isopropanol solution resulting from the extraction of the specimen ECA is taken from the essentially constant reading on the recorder. Comparison of this measured conductivity with that on the calibration curve yields the concentration of ionic contamination expressed as $\mu g$ NaCl/ml. While the conductivity is represented as the conductivity of sodium chloride, it is understood that the actual conductivity measurements are for unknown ions and not sodium chloride ions. Multiplication of the ionic contaminant concentration by the total volume of extracting solution divided by the total surface area of the specimen ECA yields the ionic contamination of the ECA in $\mu g$ NaCl/sq. in. For example, the following calculation is made:

$$\mu g\ NaCl/sq.\ in.\ =\ \frac{[\mu g\ NaCl/ml\ solution] \times [\text{volume solution } (ml)]}{\text{total surface area of } ECA\ (sq.\ in.)}$$

The following examples are illustrative of the present invention.

The following general procedures are to be followed in carrying out the determination of the amount of rosin flux and ionic residue remaining on the surface of a "cleaned" ECA. By "cleaned" ECA it is meant that the ECA has been defluxed or has been subjected to a process for removing solder flux.

EXAMPLE

General Procedure

In this example, a solution of 75 volume % HPLC grade isopropanol and 25 volume % conductivity grade water freshly obtained from a microfiltration and purification system is used. The exact total volume used need not be measured, but sufficient is used to completely fill the cartridges containing the absorbent materials plus extra to spray and recirculate without causing the pump to cavitate due to insufficient volume to maintain pump prime status. The valves to the cartridges are closed to retain the liquid in them and then the remainder of the system is drained.

A commercially available ultraviolet spectrophotometer manufactured by Micromeritics and sold under the trade name Model 787 is used in the instant examples. The spectrometer is turned on and allowed to warm up or stabilize for about 15 minutes before its use. A 200 ml sample of the 75 percent isopropanol—25 percent water is introduced to a sample chamber by means of a buret. The chamber lid is securely fastened and a circulation pump connected to the chamber is started to circulate the isopropanol solution through the chamber. An air pressure of 17-20 psi is used for the circulation pump. A high pressure pump (Waters Model 45 HPLC pump) is used to circulate a sidestream from the chamber circulation loop to the flow-cell of the spectrometer. The high pressure pump is started and its flow rate set to 3.0 ml/min. about 10 to 20 seconds after the circulation pump is started to prevent entrained air from blocking the tubing leading to the flow-cell of the ultraviolet spectrometer. The spectrometer output is set to 0.5 absorbance units full scale, which corresponds to 10 inches on a chart recorder.

The ionic conductivity is measured automatically and simultaneously by a Leeds and Northrup "7082 Series Analyzer Controller" conductivity detector fitted with a "4973 Series" conductivity cell which is located in the recirculating solution. A second pen on the dual pen recorder is used to record the results of the conductivity measurements. Alternatively, electrical resistivity could be determined rather than electrical conductivity with equivalent results since resistivity is mathematically related to conductivity as its inverse.

After 6 to 8 minutes, the recorder traces are stable. The respective Blank absorbance and the Blank conductivity are measured on the chart in inches from zero. The Blank absorbance should be near zero and the Blank conductivity $0.04 \times 10^{-6}$ mho/cm (resistance $25 \times 10^{-6}$ ohm/cm). After recording the measurement, the pumps are turned off in the reverse order from which they were turned on.

If the Blank values for absorbance and/or conductivity exceed the desired values, valves are opened to allow the solution to flow through the beds or cartridges of absorbent materials to remove organic and/or ionic contaminants until the recorded values for absorbance and conductivity have reached the predetermined desired levels. Then the valves are returned to the starting positions which causes the solution to bypass the cartridges; the best procedure is to first turn off the pumps before resetting the valves.

Calibration Curve Construction with Gum Rosin Standard Solution

After obtaining the Blank values above, the chamber is opened and exactly 5 ml of a 50 ppm standard solution is added with a buret or pipet. The 50 ppm standard solution is prepared from gum rosin and the 75 percent isopropanol/water solution. After the chamber lid is securely closed the pumps are started as described in the general procedure above. After 6 to 8 minutes, the maximum absorbance is measured in inches from zero on the chart. The pumps are then turned off. By taking the absorbance measurements after 6 to 8 minutes, the value obtained should be within 5% of the equilibrium value. The calibration curve for gum rosin is shown in FIG. 5.

Calibration Curve Construction with NaCl Standard Solution

Figure 6:
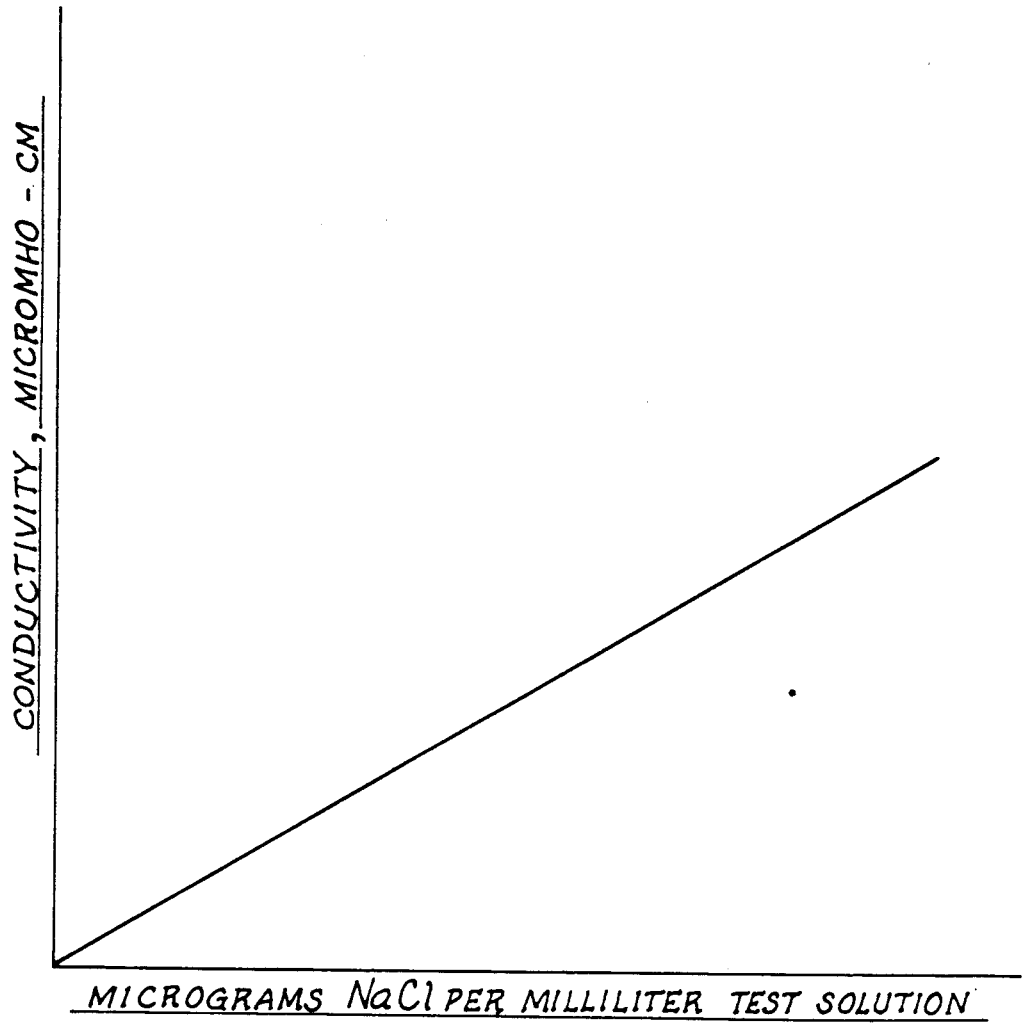
FIG. 6 represents a typical NaCl concentration vs. conductivity calibration curve.

After obtaining the Blank values above, the chamber is opened and exactly 5 ml of a 6 $\mu g$ per liter sodium chloride standard solution is added with a buret or pipet. The 6 $\mu g$ per liter standard solution is prepared from dried reagent grade sodium chloride and the 75 percent isopropanol/water solution. After the chamber lid is securely closed, the pumps are started as described in the general procedure above. After about 6 to 8 minutes, the conductivity is measured in $\mu$mho per cm. The pumps are then turned off. A calibration curve for sodium chloride is constructed using two-cycle log-log graph paper and is shown in FIG. 6.

Determination of Residues on Circuit Boards

A number of circuit boards are immersed in a commercially available rosin solder flux. The boards are allowed to dry in air for 5 to 15 minutes. Thereafter the boards are heated in an oven for 15 seconds at 240° C., to simulate the effects of a soldering process. The boards are then defluxed or cleaned by immersion for 60 seconds in a boiling defluxing solvent, for example PRELETE®, which is a blend of inhibited 1,1,1-trichloroethane and alcohol manufactured by The Dow Chemical Company, in a suitable container. When the boards have cooled in air, but within 8 hours of the defluxing step, the residual rosin flux is measured separately for each set of specimens.

The same procedures used in constructing the calibration curve described above are used herein to measure the amount of residual rosin flux and/or ionic contaminants on the boards, except that in place of the addition of an aliquot of a standard solution, a set of board specimens is placed into the chamber where it is held in place by a special insert which slides into two vertical tracks in the walls of the chamber.

After the measurement, the pumps are turned off and the set of specimens is removed from the chamber. The solution can be circulated through the cartridges of absorbent material and returned to the reservoir when sufficiently cleaned. Alternatively, the contaminated solvent is drained from the chamber and the valve left open for 3 minutes before reclosing the valve and adding the next 200 ml of isopropanol. The error in volume due to film remaining on the interior walls was determined to be less than 0.5 ml. Equilibrium values for the absorbance and/or conductivity measurements are routinely taken at approximately 6 minutes, after which time a flat horizontal maximum value should be reached. Slight drifting in the recorder trace is corrected by cleaning the spray nozzles.

What is claimed is:

1. A method for determining ionic contamination and organic contamination on an electronic circuit assembly (ECA) comprising:
    (a) contacting a previously defluxed ECA with a solvent adapted for removing ionic contaminant species and organic contaminant species on the surface of the ECA,
    (b) substantially simultaneously measuring
        (i) the spectral absorbance, in the ultraviolet or the visible wavelength range of about 190 nm to about 800 nm, of the organic contaminant species in the solvent contacted with the ECA and
        (ii) the conductivity or resistivity of the ionic contaminant species in the solvent contacted with the ECA, and
    (c) comparing the resultant absorbance measurement to a standard prepared for such comparison and comparing the conductivity measurements to a standard prepared for such comparison.

2. The method of claim 1 wherein the spectral absorbance measurement is carried out with a spectrophotometer.

3. The method of claim 2 wherein the spectrophotometer contains a flow-through cell through which the solvent passes.

4. The method of claim 1 wherein the spectral absorbance measurement is carried out with a spectrophotometer with a fiber optics probe which conducts light to the spectrophotometer.

5. The method of claim 1 wherein the conductivity or resistivity measurement is carried out with a conductivity or resistivity probe.

6. A method for substantially automatically determining ionic contamination and organic contamination on an electron circuit assembly (ECA) comprising:
    (a) substantially continuously contacting a previously defluxed ECA with a solvent adapted for removing ionic contaminant species and organic contaminant species on the surface of the ECA
    (b) substantially continuously measuring the spectral absorbance, in the ultraviolet or visible wavelength range of about 190 nm to about 800 nm, of the organic contaminant species in a continuous stream of the solvent contacted with the ECA and substantially simultaneously and continuously measuring the conductivity or resistivity of the ionic contaminant species in the solvent, and
    (c) comparing the resultant absorbance measurement to a standard prepared for such purpose and the conductivity or resistivity measurements to a standard prepared for such purpose.

7. The method of claim 6 wherein the spectral absorbance measurement is carried out with a spectrophotometer.

8. The method of claim 7 wherein the spectrophotometer contains a flow-through cell through which the solvent passes.

9. The method of claim 6 wherein the spectral absorbance measurement is carried out with a spectrophotometer with a fiber optics probe which conducts light to the spectrophotometer.

10. The method of claim 6 wherein the conductivity or resistivity measurement is carried out with a conductivity or resistivity probe.

11. The method of claim 6 wherein the solvent is isopropanol.

12. The method of claim 6 wherein the organic contaminant species is rosin.

13. A method for determining the cleanliness of an electronic circuit assembly (ECA) following defluxing to remove ionic contamination and organic contamination on the ECA which comprises
    (a) washing the previously defluxed ECA by immersion and or spraying or both spraying and immersion with a measured quantity of a solvent, said solvent having a transparency for wave lengths in the UV or visible wavelength range of about 190 nm to about 800 nm,
    (b) measuring the spectral absorbance of a stream of the wash solution by spectrometry and substantially simultaneously measuring the conductivity or resistivity of the solution,
    (c) comparing the absorbance of said wash solution with a series of standard solutions containing known amounts of the contaminant thereby to provide a calibration curve conforming to Beer's Law, $A = abc$
    A = Absorbance
    a = specific absorbance (molar absorptivity)
    b = path length of light
    c = concentration of absorbing species, and
    (d) comparing the conductivity or resistivity measurements to a standard prepared for such purpose.

14. The method of claim 13 carried out substantially automatically and continuously.

15. A method for determining the cleanliness of a printed circuit board (PCB), electronic circuit assembly (ECA), or printed wire assembly (PWA) (board) which consists of
    (a) immersing or spraying, or immersing and spraying, the board with a solvent solution;
    (b) agitating the solution, (c) measuring a stream of the solution with a calibrated spectrophotometer,
(d) measuring a stream of an uncontaminated blank with the same calibrated spectrophotometer,
(e) taking the difference between the measurements in steps (c) and (d),
(f) comparing the absorbance difference with that of a series of standard solutions containing known amounts of organic contaminant thereby to provide a calibration curve conforming to Beer's Law
A=abc
A=Absorbance
a=specific absorbance (molar absorptivity)
b=path length of light
c=concentration of absorbing species
(g) calculating the micrograms of organic contaminant in the solution according to the following formula:

$$\text{Residual organic contaminant}\left(\frac{\text{micrograms}}{\text{inch}^2}\right) = \frac{\left[\text{organic contaminant concentration}\left(\frac{\text{micrograms}}{\text{gm solvent}}\right)\right] \times \left[\begin{array}{c}\text{solvent sp.}\\\text{gr. or density}\\\text{(gm/ml)}\end{array}\right] \times \left[\begin{array}{c}\text{vol solvent}\\\text{(ml)}\end{array}\right]}{\text{total surface area of board (inch}^2\text{)}}$$

(h) measuring a stream of the solution with a conductivity probe,
(i) measuring a stream of an uncontaminated blank with the same conductivity probe,
(j) taking the difference between the measurements in steps (h) and (i),
(k) comparing the conductivity difference with a series of standard solutions containing known amounts of ionic contaminant thereby to provide a calibration curve,
(l) calculating the micrograms of ionic contaminant in the solution according to the following formula:

$$\mu\text{g NaCl/sq. in.} = \frac{[\mu\text{g NaCl/ml solution}] \times [\text{volume solution (ml)}]}{\text{total surface area of } ECA \text{ (sq. in.)}}$$

16. A method for determining the cleanliness of an electronic circuit assembly (ECA) following defluxing to remove ionic contaminants and organic contaminants on the ECA which comprises
(a) washing a previously defluxed ECA by immersion and agitation in, or by spray application of, a measured quantity of a high purity polar organic solvent or aqueous solution of said solvent, containing up to about 25 volume percent of deionized water,
(b) measuring by spectrophotometry the UV-visible absorbance, in the wavelength range of about 190 nm to about 800 nm, of a stream of said washing solution,
(c) measuring by spectrophotometry the UV-visible absorbance, in the wavelength range of about 190 nm to about 800 nm, of a stream of uncontaminated blank of the solvent,
(d) taking the difference between the two measurements in steps (b) and (c);

(e) comparing the difference in step (d) with a calibration curve developed under similar conditions by measuring known organic contaminant quantities in the solvent and plotting them on a graph, the abscissa of which is the concentration in micrograms of organic species per gram of solution or micrograms of organic species per milliliter of solution and the ordinate is the absorbance units;
(f) determining the micrograms of organic species per square inch total surface area of the ECA according to the following formula:

$$\text{Residual organic contaminant}\left(\frac{\text{micrograms}}{\text{inch}^2}\right) = \frac{\left[\text{organic contaminant concentration}\left(\frac{\text{micrograms}}{\text{gm solvent}}\right)\right] \times \left[\begin{array}{c}\text{solvent sp.}\\\text{gr. or density}\\\text{(gm/ml)}\end{array}\right] \times \left[\begin{array}{c}\text{vol solvent}\\\text{(ml)}\end{array}\right]}{\text{total surface area of board (inch}^2\text{)}}$$

(g) measuring a stream of the washing solution with a conductivity probe,
(h) measuring a stream of uncontaminated blank of the solvent with a conductivity probe,
(i) taking the difference between the two measurements in steps (g) and (h),
(j) comparing the difference in step (i) with a calibration curve developed under similar conditions by measuring known ionic contaminant quantities in the solvent and plotting then on a graph, the abscissa of which is the concentration in micrograms of ionic species per gram of solution or micrograms of ionic species per volume of solution and the ordinate is the conductivity units,
(k) determining the ionic species according to the following formula:

$$\mu\text{g NaCl/sq. in.} = \frac{[\mu\text{g NaCl/ml solution}] \times [\text{volume solution (ml)}]}{\text{total surface area of } ECA \text{ (sq. in.)}}$$

17. An apparatus for determining the ionic contamination and organic contamination of an electronic circuit assembly (ECA) comprising, in operable combination:
(a) a means for contacting a previously defluxed ECA with a solvent adapted for removing organic contaminant species on the surface of the ECA,
(b) a means for measuring the spectral absorbance, in the ultraviolet or the visible wavelength range of about 190 nm to about 800 nm, of the organic contaminant species in the solvent contacted with the ECA and substantially simultaneously measuring the conductivity of the ionic contaminant species in the solvent, and
(c) a means for comparing the resultant absorbance units to a standard prepared for such purpose and the conductivity measurements to a standard prepared for such purpose.
18. The apparatus of claim 17 wherein the means for measuring the spectral absorbance is a spectrophotometer.

19. The apparatus of claim 18 wherein the spectrophotometer contains a flow-through cell through which the solvent passes.

20. The apparatus of claim 17 wherein the means for measuring the spectral absorbance is a spectrophotometer with a fiber optics probe which conducts light to the spectrophotometer.

21. The apparatus of claim 17 wherein the means for measuring the conductivity of the ionic contaminant species is a conductivity cell.

22. An apparatus for automatically determining the ionic contamination and organic contamination of an electronic circuit assembly (ECA) comprising, in operable combination:
   (a) a means for continuously contacting a previously defluxed ECA with a solvent adapted for removing organic contaminant species on the surface of the ECA,
   (b) a means for continuously measuring the spectral absorbance, in the ultraviolet or visible wavelength range of about 90 nm to about 800 nm, of the organic contaminant series in a continuous stream of the solvent contacted with the ECA and substantially simultaneously measuring the conductivity of the ionic contaminant species in a continuous stream of the solvent, and
   (c) a means for comparing the resultant absorbance measurement to a standard prepared for such purpose and the conductivity to a standard prepared for such purpose.

23. The apparatus of claim 22 wherein the means for measuring the spectral absorbance is a spectrophotometer.

24. The apparatus of claim 23 wherein the spectrophotometer contains a flow-through cell through which the solvent passes.

25. The apparatus of claim 22 wherein the means for measuring the spectral absorbance is a spectrophotometer with a fiber optics probe which conducts the light to the spectrophotometer.

26. The apparatus of claim 22 wherein the means for measuring the conductivity of the ionic contaminant species is a conductivity cell.

27. The apparatus of claim 22 wherein the solvent is isopropanol.

28. The apparatus of claim 22 wherein the organic contaminant species is rosin.

29. An apparatus for quantitatively measuring residual ionic contaminant species and organic contaminant species on electronic circuit assemblies (ECA) comprising, in operable combination:
   (a) a vessel having a washing chamber adapted for receiving an ECA and for receiving a measured quantity of a washing solvent for washing the ECA;
   (b) a means for recirculating washing solvent to and from the vessel chamber;
   (c) a means communicating with the recirculation means for receiving a side stream of the recirculated washing solvent and cooperating means for measuring the spectral absorbance of the organic contaminant species in the side stream and cooperating means for substantially simultaneously measuring the conductivity of the ionic contaminant species in the side stream; and
   (d) means for recording the conductivity measurement and a means for recording the absorbance of the sidestream.

30. The apparatus of claim 29 including a reservoir means cooperating with said recirculation means for holding makeup washing solvent.

31. The apparatus of claim 29 including a filter communicating with said recirculation means for filtering any solid materials in the washing solvent before recirculation of the solvent to the washing chamber.

32. The apparatus of claim 29 wherein the means for recirculating the washing solvent is a pump positioned in the recirculation pattern and communicating with the means for carrying washing solvent to and from the washing chamber.

33. The apparatus of claim 29 including a means for returning the side stream to the washing solvent recirculating to the vessel after measuring the absorbance levels of the sidestream.

34. The apparatus of claim 29 including means communicating with the washing chamber for spraying washing solvent onto the ECA in the chamber.

35. The apparatus of claim 29 when enclosed within a housing.

36. The apparatus of claim 35 including a display means on the housing.

37. The apparatus of claim 29 wherein the solvent is isopropanol.

* * * * *